US012616594B2

(12) United States Patent
Hingston et al.

(10) Patent No.: US 12,616,594 B2
(45) Date of Patent: May 5, 2026

(54) GASTROINTESTINAL BYPASS DEVICES AND RELATED METHODS OF USE

(71) Applicant: Boston Scientific Scimed, Inc., Maple Grove, MN (US)

(72) Inventors: John Allen Hingston, Framingham, MA (US); Niklas Andersson, Wayland, MA (US); Moises Rivera-Bermudez, Quincy, MA (US); John B. Golden, Norton, MA (US); Andrew Calabrese, Lancaster, MA (US); Leah McElhaney, Billerica, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1283 days.

(21) Appl. No.: 17/463,281

(22) Filed: Aug. 31, 2021

(65) Prior Publication Data

US 2021/0386572 A1 Dec. 16, 2021

Related U.S. Application Data

(63) Continuation of application No. 15/611,925, filed on Jun. 2, 2017, now Pat. No. 11,129,739.

(60) Provisional application No. 62/345,254, filed on Jun. 3, 2016.

(51) Int. Cl.
*A61F 5/00* (2006.01)
*A61F 2/04* (2013.01)

(52) U.S. Cl.
CPC .............. *A61F 5/0076* (2013.01); *A61F 2/04* (2013.01); *A61F 5/0036* (2013.01); *A61F 5/0069* (2013.01); *A61F 2002/045* (2013.01); *A61F 2210/0004* (2013.01); *A61F 2220/0016* (2013.01); *A61F 2220/005* (2013.01); *A61F 2250/0069* (2013.01); *A61F 2250/0098* (2013.01)

(58) Field of Classification Search
CPC .... A61F 5/0076; A61F 5/0036; A61F 5/0069; A61F 2/04; A61F 2002/045; A61F 2210/0004; A61F 2210/0014; A61F 2220/0016; A61F 2220/005; A61F 2250/0069; A61F 2250/0098
See application file for complete search history.

(56) References Cited

U.S. PATENT DOCUMENTS

| | | | | |
|---|---|---|---|---|
| 8,517,972 | B2 * | 8/2013 | Graham | A61F 5/0079 604/8 |
| 8,579,849 | B2 * | 11/2013 | Grau | A61F 5/0089 604/9 |
| 8,652,083 | B2 * | 2/2014 | Weitzner | A61F 2/04 623/23.65 |
| 8,801,650 | B2 * | 8/2014 | Gannoe | A61B 17/072 623/23.65 |
| 9,421,116 | B2 * | 8/2016 | Aramaki | A61F 5/0076 |

(Continued)

*Primary Examiner* — Philip R Wiest
(74) *Attorney, Agent, or Firm* — Bookoff McAndrews PLLC

(57) ABSTRACT

A bypass device may include an elongate member extending from a proximal end toward a distal end, and a proximal opening and a distal opening coupled to one another by a lumen disposed through the elongate member. The bypass device also may include at least one port extending through a side surface of the elongate tubular member, wherein at least a portion of the bypass device may be bioabsorbable.

13 Claims, 4 Drawing Sheets

(56)     References Cited

U.S. PATENT DOCUMENTS

| | | | | |
|---|---|---|---|---|
| 9,480,590 | B2 * | 11/2016 | Ortiz ..................... | A61F 5/0076 |
| 9,707,116 | B2 * | 7/2017 | Bangera .................. | A61L 27/54 |
| 2004/0107004 | A1 * | 6/2004 | Levine ................... | A61F 2/848 |
| | | | | 623/1.13 |
| 2005/0085923 | A1 * | 4/2005 | Levine ................. | A61F 5/0089 |
| | | | | 623/23.65 |
| 2008/0208357 | A1 * | 8/2008 | Melanson ............. | A61F 5/0076 |
| | | | | 623/23.65 |
| 2009/0012544 | A1 * | 1/2009 | Thompson .......... | A61B 17/1114 |
| | | | | 606/156 |
| 2011/0307070 | A1 | 12/2011 | Clerc et al. | |
| 2012/0116528 | A1 * | 5/2012 | Nguyen ................... | A61F 2/04 |
| | | | | 623/23.7 |
| 2012/0150094 | A1 * | 6/2012 | Gannoe ................ | A61F 5/0079 |
| | | | | 604/8 |
| 2013/0018452 | A1 * | 1/2013 | Weitzner ................... | A61F 2/88 |
| | | | | 623/1.15 |
| 2014/0243950 | A1 | 8/2014 | Weiner | |
| 2015/0258253 | A1 * | 9/2015 | Fater .................... | A61L 31/145 |
| | | | | 427/2.24 |
| 2015/0374484 | A1 * | 12/2015 | Hingston .............. | A61M 39/24 |
| | | | | 623/23.65 |
| 2016/0022253 | A1 * | 1/2016 | Khanchandani ............................ | |
| | | | | A61B 17/00491 |
| | | | | 606/214 |

* cited by examiner

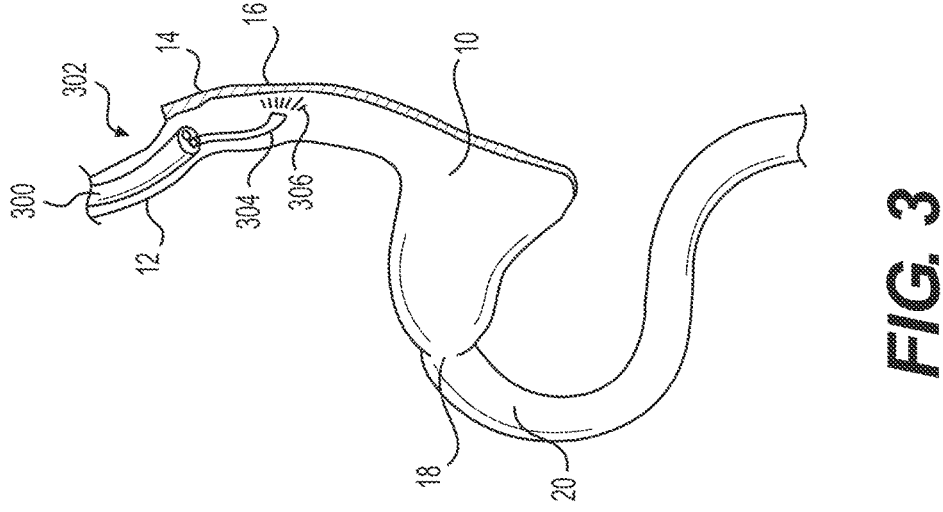
*FIG. 1*
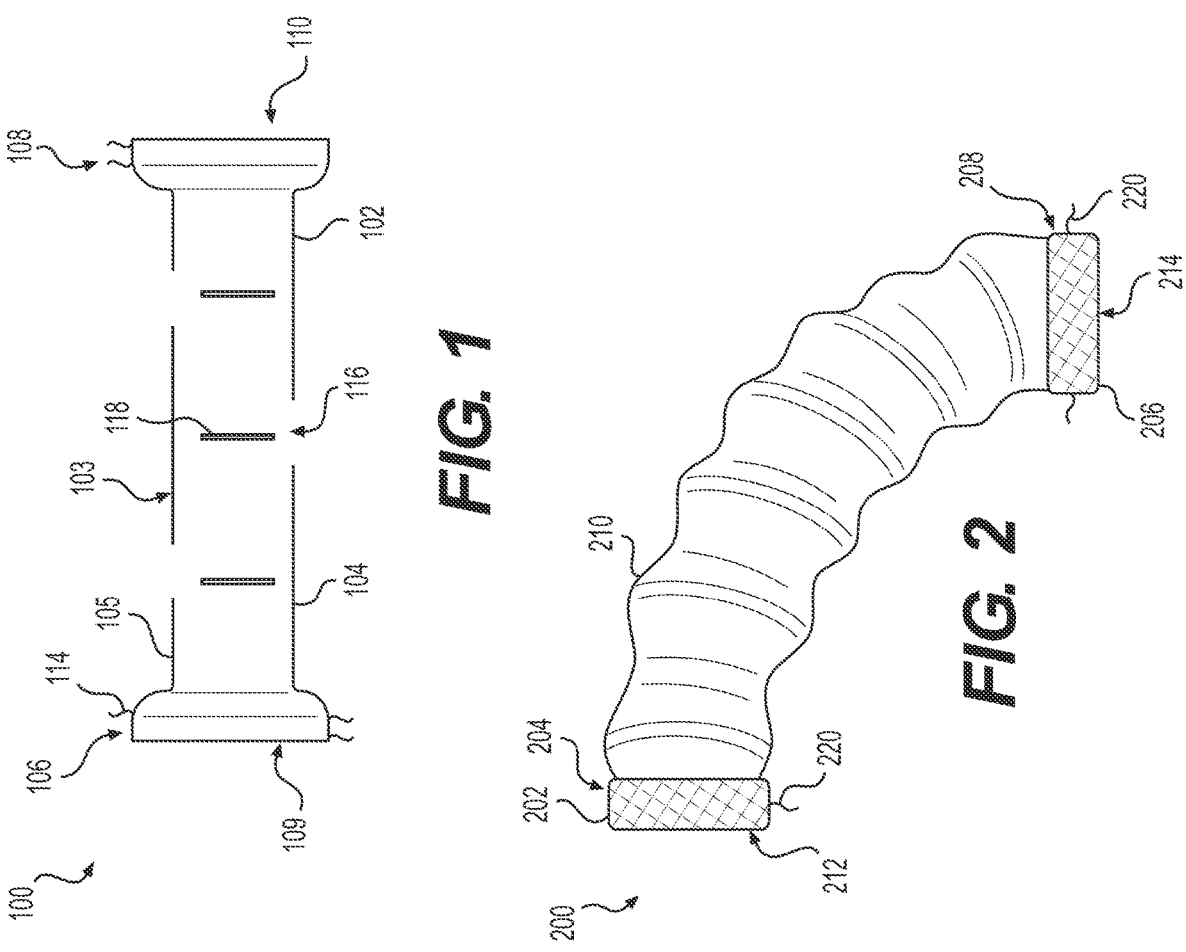
*FIG. 3*
*FIG. 2*

GASTROINTESTINAL BYPASS DEVICES AND RELATED METHODS OF USE

CROSS-REFERENCE TO RELATED APPLICATION(S)

This patent application is a continuation of U.S. patent application Ser. No. 15/611,925, filed on Jun. 2, 2017, which claims the benefit under 35 U.S.C. § 119 to U.S. Provisional Patent Application No. 62/345,254, filed on Jun. 3, 2016, the entireties of which are incorporated herein by reference.

TECHNICAL FIELD

Examples of the present disclosure relate to gastrointestinal bypass devices and related methods of use.

BACKGROUND

Obesity is a medical condition in which excess body fat has accumulated to the extent that it may have an adverse effect on health, leading to reduced life expectancy and/or increased health problems. Body mass index (BMI), a measurement which compares weight and height, defines people as overweight (pre-obese) when their BMI is between 25 kg/m² and 30 kg/m², and obese when it is greater than 30 kg/m². Obesity is most commonly caused by a combination of excessive dietary calories, lack of physical activity, and genetic susceptibility. On average, obesity may reduce life expectancy by six to seven years. Obesity also increases the likelihood of various diseases, particularly heart disease, type 2 diabetes, breathing difficulties during sleep, certain types of cancer, and osteoarthritis. Obesity is a leading preventable cause of death worldwide, with increasing prevalence in adults and children.

Bariatric (or weight loss) surgeries are surgical treatments for treating severe obesity, and may involve removal of a portion of the stomach or a reduction in the size of the stomach (e.g., in a sleeve gastrectomy). These procedures can be effective but also have associated risks.

After such procedures, patients may be at risk for developing a post-surgical leak. On their own, leaks can complicate recovery, but they are more severe for patients who have compromised immune systems or multiple co-morbidities. Leaks can even cause sepsis and death. Furthermore, leaks are costly to treat, and some patients cannot safely withstand another surgery.

Esophageal stents have been used to treat leaks after sleeve gastrectomy. Esophageal stents, however, are prone to migration because their shapes are not adapted to the modified stomach geometry after sleeve gastrectomy. Two esophageal stents are often employed because existing stents are too short for a successful treatment.

Thus, a need exists for a minimally-invasive, endoscopic approach for reducing risks associated with post-surgical leaks.

SUMMARY

In one aspect, the present disclosure is directed to a bypass device, which may include an elongate member extending from a proximal end toward a distal end, and a proximal opening and a distal opening coupled to one another by a lumen disposed through the elongate member. The bypass device also may include at least one port extending through a side surface of the elongate tubular member, wherein at least a portion of the bypass device may be bioabsorbable.

The elongate member may be a stent defining proximalmost and distalmost portions of the bypass device. The bypass device may include a coating disposed over an outer surface of the stent, wherein the coating may be impermeable to liquid. The coating may include a bioadhesive. An outer surface of the elongate member may include one or more anchoring features configured to pierce or grab tissue. The one or more anchoring features may be bioabsorbable. The elongate member may be biologically-stable. An entirety of the bypass device may be bioabsorbable. The proximal end and the distal end of the elongate member each may have a larger cross-sectional dimension than an intermediate portion of the elongate member.

In another aspect, the present disclosure is directed to a bypass device, which may include a proximal anchor having an opening, a distal anchor having an opening, and a membrane sleeve disposed between the proximal anchor and the distal anchor, wherein the opening of the proximal anchor and the opening of the distal anchor may be fluidly coupled to one another via the membrane sleeve, wherein at least one of the proximal anchor, the distal anchor, and the membrane sleeve may be bioabsorbable.

Each of the proximal anchor, the distal anchor, and the membrane sleeve may be bioabsorbable. The membrane sleeve may be bioabsorbable, and the proximal anchor and the distal anchor may be biologically-stable. A interior of the proximal anchor and the distal anchor each may include a material configured to inhibit tissue in-growth. The proximal anchor and the distal anchor may be self-expanding, and each may be configured to exert a radially outward force when compressed. One or more of the proximal anchor and the distal anchor may include one or more anchoring features on a respective outer surface, wherein the one or more anchoring features may configured to pierce or grab tissue.

In yet another aspect, the present disclosure is directed to a method of treating a surgically-modified stomach of a patient. The method may include applying an adhesive to the post-surgical leak site or to a staple line of the surgically-modified stomach to form an adhesive plug, and expanding a bypass device in the stomach to apply a radially outward force against the adhesive and to tissue surrounding the bypass device.

The surgically-modified stomach may have been subject to a sleeve gastrectomy procedure. Liquids and solids ingested by the patient may be diverted through the bypass device, and may be prevented from contacting the post-surgical leak site. The bypass device may be a covered stent. At least a portion of the covered stent may be bioabsorbable.

BRIEF DESCRIPTION OF THE DRAWINGS

The accompanying drawings, which are incorporated in and constitute a part of this specification, illustrate various examples and together with the description, serve to explain the principles of the disclosed examples.

FIG. 1 is a side view of a bypass device according to an example of the present disclosure.

FIG. 2 is a side view of a bypass device according to another example of the present disclosure.

FIGS. 3 and 4 illustrate a method of treating a patient after a sleeve gastrectomy, according to an example of the present disclosure.

Figure 4:
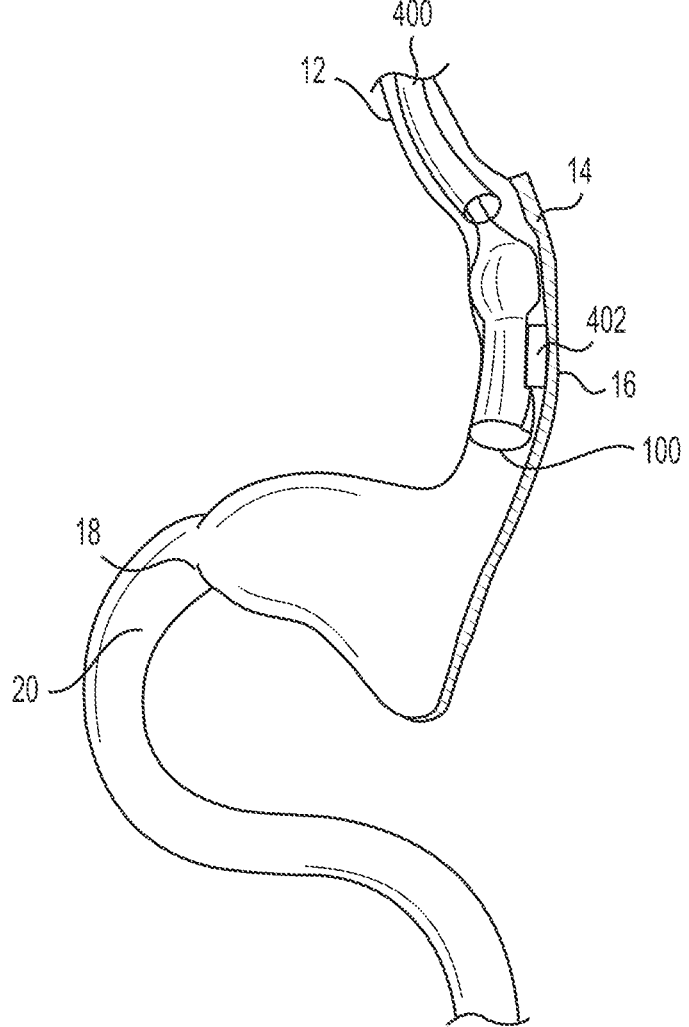

As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal."

DETAILED DESCRIPTION

Reference will now be made in detail to examples of the present disclosure, which are illustrated in the accompanying drawings. Wherever possible, the same reference numbers will be used throughout the drawings to refer to the same or like parts or components. The term "distal" refers to the direction that is away from the user or operator and into the patient's body. By contrast, the term "proximal" refers to the direction that is closer to the user or operator and away from the patient's body.

In at least some examples, the present disclosure is directed to systems, devices, and methods used to bypass portions of the body (e.g., a staple line in a surgically-modified stomach) that are prone to post-surgical leaks. Most of the leaks occurring after a sleeve gastrectomy are found in the upper part (e.g., the proximal third) of the newly-formed stomach "sleeve." This occurs because the upper part of the stomach is less accessible during surgery and more difficult to staple. In at least one example, a staple line or leak site inside a surgically-modified stomach may be bypassed. That is, food and/or liquid ingested by a patient may travel down the esophagus, and may be diverted around the staple line and/or leak site through a bypass device implanted into the patient. This may prevent ingested liquids or solids from reaching the staple line and/or leak site, and from leaking into the abdominal cavity. Such leaks may be post-anastomosis surgical leaks. The disclosed devices and methods may isolate the staple line, offering resistance to any form of leakage at that region. Such isolation may enable the staple line to be repaired and healed naturally over time, and reduce the risk of infection. The ingested liquids and/or solids may exit the bypass device and enter a portion of the stomach downstream of the staple line, or may exit the bypass device directly into the duodenum or another portion of the small intestine.

FIG. 1 is a side view of one example of a bypass device, e.g., a stent 100 according to the disclosure. Stent 100 may include an elongated tubular stent frame 102, which may be entirely, substantially or partially, covered with a covering or coating 104. More particularly, coating 104 may be disposed over an outer surface 105 of the stent frame 102. Stent 100 may extend from a proximal end 106 to a distal end 108. In some examples, one or more of proximal end 106 and distal end 108 may be flared. That is, the proximal end 106 and/or distal end 108 may have a larger diameter than an intermediate, elongate tubular section 103. The larger diameter or cross-sectional dimension may help secure proximal end 106 and/or distal end 108 in respective body lumens. It is also contemplated that proximal end 106 and distal end 108 may not be flared, and may have substantially similar cross-sectional dimensions as elongate tubular section 103.

Stent 100 also may include a proximal opening 109 and a distal opening 110. Liquid and/or solids may enter stent 100 via proximal opening 109, and may exit stent 100 via distal opening 110. Proximal opening 109 and distal opening 110 may be fluidly coupled to one another by a lumen extending through stent 100.

Stent frame 102 may be generally cylindrical in shape, or may have another suitable shape or cross-section. In some examples, stent frame 102 may be substantially flexible, while in other examples, stent frame 102 may be substantially rigid. In some examples, the flared proximal end 106 and the flared distal end 108 may be configured to contact corresponding body lumens to prevent passage of food or liquid between stent 100 and the corresponding body lumen wall. It is contemplated that various shapes, sizes and designs of stent frame 102 may be constructed depending on the size and geometry of the lumens and cavities where the stent 100 will be placed. Stent frame 102 may have a woven structure fabricated from a number of filaments, may be braided and include only one filament, or may be braided with several filaments. In still further examples, the stent frame 102 may be knitted, knotted, or laser cut.

Stent frame 102 can be made from a number of different materials such as, but not limited to, metals, metal alloys, shape memory alloys, and/or polymers, as desired, enabling the stent 100 to be expanded when positioned within the body. In some examples, stent frame 102 may be formed from alloys such as, e.g., nitinol and elgiloy.

Depending the on material selected for construction, stent 100 may be self-expanding. That is, once stent 100 is urged from the distal end of a delivery device, e.g., catheter 400 shown in FIG. 4, stent 100 may expand radially outward from a compressed, delivery configuration. Alternatively, stent 100 may not be self-expanding, and may be expanded by other mechanisms. In one example, stent 100 may be expanded by a balloon inserted into the stent 100. The balloon may be expanded by application of pressure, and/or heat may be applied to the body of stent 100 to facilitate its expansion. Once expanded to a desired state, the stent 100 may be allowed to cool and set, while the expanded size of the balloon is maintained in order to form the desired shape of the stent 100. Next, the balloon may be deflated by removing the application of pressure, and the balloon may be removed from the stent 100. In other examples, an expandable basket or other suitable expandable member may be used to expand the stent 100.

The coating 104 disposed on the outer surface 105 of the stent frame 102 may be resistant to degradation. Additionally, the coating 104 may prevent liquids and solids from passing through openings in the outer surface 105 of the stent frame 102 (e.g., when stent frame 102 is a mesh), and into the stomach and any post-surgical leaks that may exist. Thus, coating 104 may restrict ingested liquids and solids from undesirably passing through the outer surface 105 of the stent frame 102, which may occur in the absence of the coating 104. Further, the coating 104 may be applied throughout the structure of stent 100, and may be configured to accommodate the bends and flexures that may occur during transfer and deployment of stent 100. To this end, coating 104 may include a material that swells. Additionally, coating 104 may inhibit tissue in-growth onto stent 100, which may otherwise complicate stent removal once any post-surgical leaks have healed. In some examples, stent 100 may be left within the body from two weeks to eight weeks, although longer and shorter time frames are also contemplated. In further examples, stent 100 may be biodegradable after a predetermined period of time.

In various examples, coating 104 may include silicone, styrene isoprene butadiene (SIBS), expanded polytetrafluoroethylene (ePTFE or expanded Teflon®), polyurethane, or another suitable polymer. Coating 104 also may include growth factors, proteins and/or steroids to promote healing of tissue that comes into contact with coating 104. Examples of substances that promote healing include growth factors (TGF-alpha, platelet derived growth factor), endothelial progenitor cells, fibroblasts and retinoids.

The outer surface 105 of stent 100 may be roughened, textured, notched, slotted, etched, sand-blasted, coated or otherwise modified to provide a better gripping surface. The outer surface 105 also may include features that increase the surface area of the outer surface 105 to promote drug delivery into the mucosa lining the stomach, such as, e.g., micro-needles, micro-pores, micro-cylinders, micro-cones, micro-pyramids, micro-tubes, micro-parallelepipeds, micro-prisms, micro-hemispheres, teeth, ribs, ridges, or the like. In some examples, the entirety of the stent 100, and not just the outer surface 105, may include one or more of these features.

Stent 100 may include one or more anchoring features, such as anchoring features 114 that are configured to help anchor stent 100. The anchoring features 114 may be any suitable shape, such as, e.g., a barb, spike, or other suitable shape that is configured to pierce through tissue or otherwise grab tissue to prevent migration of the stent 100 while implanted in a body lumen. Anchoring features 114 may extend radially outward from the outer surface 105 of stent 100, and may be both longitudinally and radially staggered from one another.

In addition to, or as an alternative to anchoring features 114, the outer surface of stent 100 may be coated with a bioadhesive to help anchor stent 100 within a body lumen. In some examples, the bioadhesive material(s) may include, but are not limited to, fibrinogen, amino adhesives, adhesive surface proteins (MSCRAMMS), adhesively modified biodegradable polymers such as Fatty Ester Modified PLA/PLGA, polymer materials, minigel particles, or other suitable bioadhesives. MSCRAMMS may include materials naturally-produced by pathogens to initiate adhesion to the host extracellular matrix to initiate infection. These adhesive surface proteins may be isolated or synthesized, and utilized to facilitate adhesion of stent 100 within a body lumen.

The bioadhesive material may be dissolved in a solvent or co-solvent blend prior to application to the outer surface of stent 100. The solvent may include alcohols (e.g., methanol, ethanol, and isopropanol), water, or another suitable solvent.

Amino acid bioadhesives may be utilized to facilitate adhesion of the outer surface 105 to a target location in the body. Zwitterionic amino acids may be employed as a layer or as a component of the outer surface. In one example, the amino acid 3,4-L-dihydroxyphenylalanine (DOPA), which is a tyrosine derivative found in high concentrations in the glue proteins of mussels, may be utilized.

Adhesively modified biodegradable polymers may include DOPA (L-3,4-dihydroxyphenylalanine) modified PLA (polylactic acid), PLGA poly(lactic-co-glycolic acid), among others. In such examples, examples of suitable adhesive moieties include, but are not limited to, monopalmitate, monostearin, glycerol, dilaurin, iso-stearyl alcohol, or the like.

Other polymer materials may alternatively be utilized as bioadhesives, including, but not limited to, proteins (e.g., gelatin) and carbohydrates (e.g., starch). For example, polysaccharides such as sorbitol, sucrose, xylitol, anionic hydrated polysaccharides (gellan, curdlan, XM-6, and xanthan) may also be employed as a bioadhesive. Other suitable materials include derivatives of natural compositions such as algenic acid, hydrated gels and the like, and also biocompatible polymers and oligomers such as dextrans, dextranes, dextrins, hydrogels including, but not limited to, polyethylene glycol (PEG), polyethylene glycol/dextran aldehyde, polyethylene oxide, polypropyline oxide, polyvinylpyrrolidine, polyvinyl acetate, polyhydroxyethyl methacrylate, and polyvinyl alcohol, as well as derivatives thereof may also be employed herein.

Minigel particles may additionally or alternatively be utilized as a bioadhesive. One exemplary bioadhesive is poly(NIPAM) (poly(N-isopropylacrylamide)) minigel particles. Poly(NIPAM) may be in a liquid state at room temperature, and an adhesive at body temperature. Additionally, for improved retention of the polymer on the outer surface 105, minigel particles may be crosslinked or mixed with a higher molecular weight polymer to allow enough time for retention of the minigel to the stent during delivery, or uncrosslinked minigel particles can be employed in a crosslinked polymer network.

In an alternative example, some or all of stent 100 may be formed from a bioabsorbable material. According to one example, at least one portion of stent 100 may include one or more commercially available grades of polylactide, poly-L-lactide (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester, poly(amino acids), poly(alpha-hydroxy acid), collagen or other connective proteins or natural materials, polycaprolactone, and copolymers of these materials as well as composites thereof and combinations of other biodegradable polymers.

In one example, the entirety of stent 100 (including stent frame 102 and anchoring features 114) may be formed of a bioabsorbable material. In another example, only anchoring features 114 may be formed of a bioabsorbable material, while a remainder of the stent 100 is formed from a non-bioabsorbable, or otherwise biologically-stable material. In these examples, the bioabsorbable anchoring features 114 may prevent migration of an implanted stent 100. However, since treatment (e.g., bypass) may be only desired for a finite period of time, a medical practitioner may remove a remaining, biologically-stable portion of stent 100 in a subsequent procedure. When the anchoring features 114 are bioabsorbable, they may degrade prior to removal of the stent 100, potentially reducing the amount of damage to the stomach wall, esophagus, pylorus, or other body lumen or cavity, when the stent 100 is removed. When the anchoring features 114 are formed from non-bioabsorbable materials, removing a stent 100 having anchoring features 114 embedded into the tissue may cause damage to the tissue (e.g., tearing and puncturing of the tissue).

Stent 100 also may include one or more ports 116 that are disposed on a circumferential side surface of the stent 100. The ports 116 may thus be different than the proximal opening 109 and distal opening 110 of stent 100 disposed at proximal end 106 and distal end 108, respectively. Ports 116 may permit the passage of materials and devices from within the stent 100 to a volume disposed outside of the stent 100. In some examples, one or more of ports 116 may include a rubber or rubber-like septum to allow the passage of, e.g., a needle through the ports 116, but that prevents the passage of fluids between volumes interior and exterior to the ports 116. Ports 116 may include any other suitable mechanism that may transition ports 116 from an open configuration, in which materials may move freely between the interior and exterior of the stent 100, and a closed configuration, in which materials may not move between the interior and the exterior of stent 100. In other examples, ports 116 may always be open (i.e., do not have an associated structure for closing the port 116). In examples where ports 116 are always open, during expansion of stent 100, such ports 116 may be positioned against locations in the stomach that have a very low chance of containing a post-surgical leak. Stent 100 also may include multiple ports 116, which may be longitudinally and/or circumferentially staggered from one another to permit a medical practitioner to access spaced apart locations in a body lumen or cavity via the various ports 116.

Stent 100 may include one or more radiopaque markers 118, which may be aligned with the one or more ports 116. The radiopaque markers 118 may be arranged over the length of the stent 100, as shown, and each radiopaque marker 118 may correspond to a longitudinal position of a respective port 116. While there are three separate radiopaque markers 118 illustrated in FIG. 1, it is contemplated that there may be any number of radiopaque markers 118 as desired, such as, but not limited to, zero, one, two, three, four, or more. Further, the radiopaque markers 118 may positioned at any other suitable location on the stent 100, and may not necessarily be aligned with a port 116. In some examples, the entire stent 100 may be coated with a radiopaque material to facilitate fluoroscopic positioning.

FIG. 2 is a side view of another example of a bypass device 200 according to the disclosure. Bypass device 200 may include a proximal anchor 202 disposed at a proximal end 204, and a distal anchor 206 disposed at a distal end 208. A sleeve 210 may be disposed between the proximal anchor 202 and the distal anchor 206. Bypass device 200 also may include a proximal opening 212 and a distal opening 214. Proximal opening 212 may be in fluid communication with distal opening 214 via sleeve 210. Liquid and/or solid food particles may enter bypass device 200 via proximal opening 212, pass through sleeve 210, and exit bypass device 200 through distal opening 214.

Anchors 202 and 206 may be expandable members configured to be positioned in a body lumen. Anchors 202 and 206 may be formed of substantially the same materials used to form stent 100 as described above. Thus, anchors 202 and 206 may be stent-like members having a coating 216 disposed on an outer surface thereof. Coating 216 may include any of the materials described above with reference to coating 104, including, e.g., bioadhesives and the like. One or more of anchors 202 and 206 also may include one or more anchoring features 220, which may be substantially similar to anchoring features 114 described above. Anchors 202 and 206 also may include other surface features described with reference to stent 100 that help prevent migration of anchors 202 and 206 inside the body.

Sleeve 210 may be formed from a polymer material, such as, e.g., an elastomeric polymeric material. Examples of polymers that could be used to form sleeve 210 include Teflon®, PTFE, FEP, polyethylene and polypropylene, silicone, polyurethane and polyether-block-amide, among others. Sleeve 210 may be a flexible, floppy, compliant, and/or impermeable membrane. That is, sleeve 210 may have a sheet-like structure configured to collapse upon itself when no outside forces are applied to the sleeve 210. In some examples, sleeve 210 may include an elastic and/or resilient material.

It is also contemplated that one or more of anchor 202, anchor 206, and sleeve 210 may be formed from a bioabsorbable material. In one example, each of anchor 202, anchor 206, and sleeve 210 are formed from bioabsorbable materials so that once inserted, no subsequent procedure is required to remove the bypass device 200. In yet another example, sleeve 210 is formed from bioabsorbable materials, while anchors 202 and 206 are formed from biologically-stable materials. In this example, a subsequent procedure may still not be required to retrieve bypass device 200 from the body. That is, once sleeve 210 is bioabsorbed or biodegrades, the stomach may function normally with liquids and solids passing through the anchors 202 and 206. In yet another example, each of anchor 202, anchor 206, and sleeve 210 are formed from biologically stable materials, and bypass device 200 may be retrieved after enough time has elapsed for any post-surgical leaks in the staple line to heal.

FIGS. 3 and 4 illustrate a method of repairing post-surgical leaks in a surgically-modified stomach, and subsequently bypassing the post-surgical leaks via a bypass device. The stomach 10 illustrated in FIG. 3 may be a surgically resected stomach after a sleeve gastrectomy. An esophagus 12 is shown leading to the stomach 10. The interior of stomach 10 may include a staple line 14 and a leak site 16. The pyloric sphincter 18 is shown coupling the stomach to the duodenum 20.

In some examples, a leak site 16 may be identified by any suitable mechanism including, e.g., visual inspection, contrast studies, or other suitable mechanisms. An elongate member, such as, e.g., an endoscopic member 300, then may be inserted through the esophagus 12 and into the stomach 10. A catheter 304 may extend distally from a distal end 302 of the endoscopic member 300, and may be used to deliver an adhesive 306 to leak site 16. In other examples, catheter 304 may extend radially from a side surface of endoscopic member 304. In yet another example, adhesive 306 may be delivered directly from a lumen of endoscopic member 300. In one example, adhesive 306 may include sealants with suitable bonding properties, elasticity, and biodegradability for use in a patient. Examples of adhesive 306 include, e.g., cyanoacrylate, collagen, fibrinogen with or without thrombin, fibrin, fibrin glue, fibropectin, elastin, laminin, polyacrylic acid, polystyrene, polymers derivatized with arginine, polymers derivatized with glycine, polymers derivatized with aspartic acid, and copolymers, which may be sprayed, injected, otherwise delivered by catheter 304 onto leak site 16 to facilitate occlusion, closure, and/or healing of leak site 16.

Referring to FIG. 4, the applied adhesive 306 may form an adhesive plug 402 of material along the mucosa of the stomach. The nature of the mucosa may make it difficult for any adhesive or sealant to remain in place within the stomach. The mucosa is a moist environment, and, on its own, a plug 402 may not remain in position along the mucosa for long enough to allow a leak site 16 to properly heal. Thus, a stent or other expandable member 100 may be utilized to help maintain plug 402 adjacent to or otherwise in contact with leak site 16. Thus, once plug 402 is formed, a delivery device, e.g., catheter 400 may be inserted into the stomach 10 via esophagus 12. Then, stent 100 may be urged from the distal end of catheter 400, and may be expanded radially outward such that stent 100 applies a radially outward force against the stomach wall and plug 402. As set forth above, stent 100 may self-expand upon exiting the catheter 400, or may be expanded by, e.g., a balloon or basket member. The radially outward force may help maintain the position of plug 402 adjacent to or otherwise in contact with leak site 16, promoting the healing of leak site 16. Additionally, fluid may be prevented from reaching leak site 16 and/or any portion of staple line 14 based on the positioning of stent 100. That is, the proximal and distal ends of stent 100 may expand and be flush against tissues defining a respective body lumen, thereby forcing fluid into stent 100 to prevent the ingested fluid from reaching leak site 16. The proximal end of stent 100 may be positioned in the esophagus 12 or in a position that is proximal to leak 16 or staple line 14. The distal end of stent 100 may be positioned in the pyloric sphincter 18 or in a position that is distal to leak site 16 and/or staple line 14.

With plug 402 and stent 100 in place, ingested fluids and solids may bypass leak site 16 and/or staple line 14, permitting leak site 16 and staple line 14 to heal with reduced risks for post-surgical complications. After a suitable period of time for leak 16 and staple line 14 to heal, e.g., two weeks to eight weeks, stent 100 may be removed by a medical practitioner in a subsequent medical procedure. Alternatively, when stent 100 is bioabsorbable, stent 100 may be resorbed into body tissues, and no subsequent retrieval procedure may be necessary.

Figure 5:
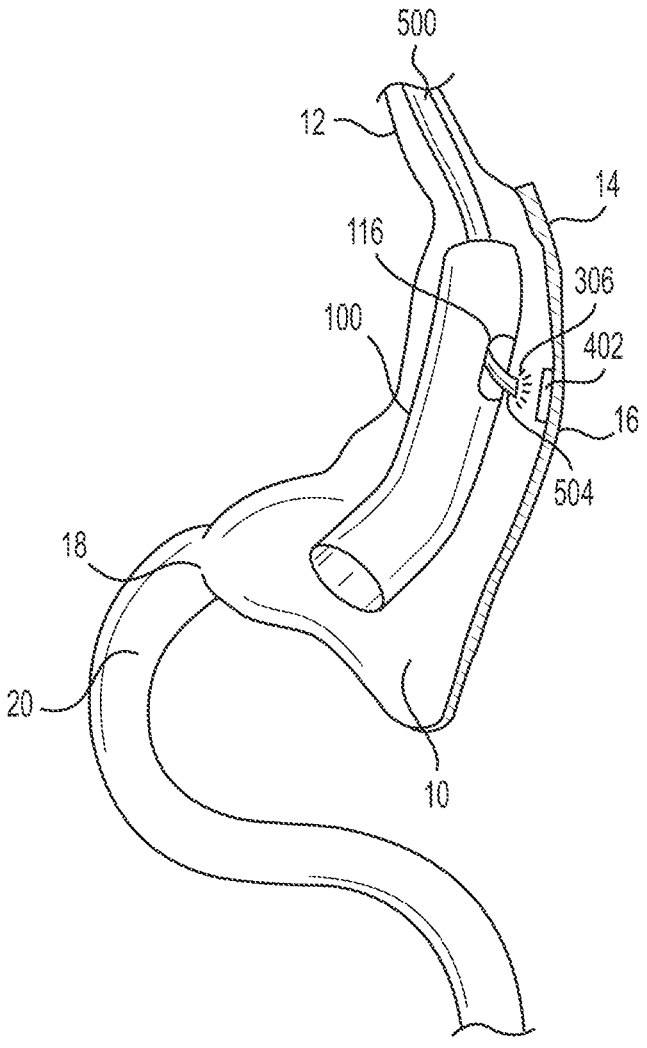
FIG. 5 illustrates a method of treating a patient after a sleeve gastrectomy, according to another example of the present disclosure.

FIG. 5 illustrates another method of repairing post-surgical leaks in a stomach. Once a leak site 16 has been detected, a delivery member 500 may be inserted into the stomach 10 via esophagus 12. In this example, stent 100 may be disposed on a distal end of delivery member 500, and may be expanded by an expanding portion of delivery member 500 disposed within stent 100, such as, e.g., a balloon and/or a basket. Further, a catheter 504 may be extended through a side port 116 of stent 100 to deliver adhesive 306 to leak site 16 to form a plug 402. In other examples, one or more of the pro-healing materials described above may be delivered to leak site 16 via side port 116. Once the plug 402 is formed, stent 100 may be radially expanded to provide a radially outward force against the stomach wall and plug 402 in order to help maintain the position of plug 402 adjacent to or otherwise in contact with the leak site 16. Stent 100 may be expanded such that a closed wall portion (i.e., a portion of stent 100 not including port 116) is brought into contact with plug 402, in order to prevent plug 402 from receding into the interior volume of stent 100.

Figure 6:
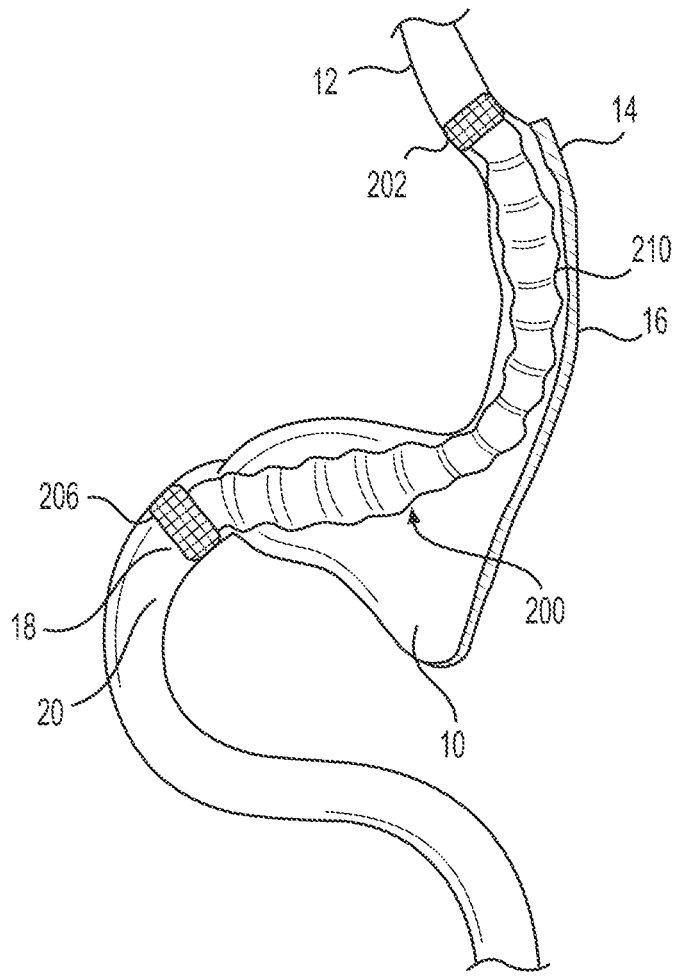
FIG. 6 illustrates a method of treating a patient after a sleeve gastrectomy, according to yet another example of the present disclosure.

FIG. 6 illustrates a bypass device 200 implanted in a patient. The proximal anchor 202 may be positioned in a distal portion of the esophagus 12 proximate to the gastroesophageal junction, or may be positioned in the gastroesophageal junction. Anchor 202 may apply a radially outward force against, e.g., the esophagus 12, and ingested liquids and solids may be forced to enter the bypass device 200. The ingested liquids and solids then may travel through sleeve 210, and may exit bypass device 200 through distal anchor 206. The distal anchor 206 may be positioned in the pyloric sphincter 18 downstream of the staple line 14 and/or leak site 16. The positioning of proximal and distal anchors 202 and 206 may divert ingested fluid and liquid away from staple line 14 and/or leak site 16, allowing the staple line 14 and/or leak site 16 to heal naturally. After a suitable period of time, bypass device 200 may be retrieved in a subsequent medical procedure. Alternatively, when one or more portions of bypass device 200 are bioabsorbable, a subsequent procedure may not be necessary.

Those skilled in the art will understand that the bypass devices set out above can be implemented in any suitable body lumen (e.g., blood vessels, the biliary tract, urological tract, gastrointestinal lumens, and the like) without departing from the scope of the disclosure as defined by the claims. In particular, constructional details, including manufacturing techniques and materials, are well within the understanding of those of skill in the art and have not been set out in any detail here. These and other modifications and variations are well within the scope of the present disclosure and can be envisioned and implemented by those of skill in the art. Any feature described herein with respect to a given example may be used in conjunction with any other disclosed example.

Other examples of the present disclosure will be apparent to those skilled in the art from consideration of the specification and practice of the examples disclosed herein. It is intended that the specification and examples be considered as exemplary only, and departures in form and detail may be made without departing from the scope and spirit of the present disclosure as defined by the following claims.

What is claimed is:

1. A stent, comprising:

a tubular frame having a proximal end opposite a distal end, wherein a lumen extends between the proximal and distal ends, the tubular frame comprising:

a flared section at the proximal end, wherein the flared section includes a sloped portion;

a plurality of anchoring features extending radially outward from an outer surface of the proximal end, wherein the plurality of anchoring features are located adjacent to the sloped portion of the flared section, wherein each of the plurality of anchoring features are both longitudinally and radially staggered from adjacent anchoring features;

an intermediate section extending from the flared section and positioned between the proximal and distal ends, wherein a diameter of the flared section is greater than a diameter of the intermediate section, wherein the intermediate section includes a plurality of ports extending through the intermediate section, and wherein the intermediate section includes a plurality of radiopaque markers corresponding to a position of each of the plurality of ports; and a coating extending partially along a surface of the tubular frame, and configured to inhibit tissue ingrowth into the stent, wherein the coating is spaced apart from the plurality of anchoring features of the flared section to promote tissue ingrowth at the flared section.

2. The stent of claim 1, wherein the coating is spaced apart from a second plurality of anchoring features to promote tissue ingrowth with the intermediate section.

3. The stent of claim 2, wherein the second plurality of anchoring features are provided on the distal end, and wherein the distal end has a diameter greater than the diameter of the intermediate section.

4. The stent of claim 3, wherein the coating is spaced from the distal end to promote tissue ingrowth with the distal end.

5. The stent of claim 1, wherein the sloped portion extends away from a central longitudinal axis extending through the lumen and the intermediate section.

6. The stent of claim 1, wherein the intermediate section has a substantially uniform diameter.

7. The stent of claim 1, wherein the tubular frame is formed by a plurality of filaments interwoven with one another to form one or more of the proximal end, the intermediate section, and the distal end.

8. The stent of claim 1, wherein the plurality of ports are positioned such that a longitudinal position and a circumferential position of each of the plurality of ports are offset from longitudinal positions and circumferential positions of adjacent ports.

9. The stent of claim 1, wherein each of the plurality of radiopaque markers are positioned in longitudinal alignment with at least one of the plurality of ports.

10. A method, comprising:

deploying a system within a gastrointestinal (GI) tract of a patient, the system comprising:

a stent comprising:

a tubular frame having a first end opposite a second end, wherein a lumen extends between the first and second ends, and wherein the tubular frame comprises:

a flared section at one of the first or second ends;

an intermediate section extending from the flared section, wherein a diameter of the flared section is greater than a diameter of the intermediate section;

a plurality of ports extending through the intermediate section, each of the plurality of ports having a radiopaque marker corresponding to a position of each respective port; and a coating extending partially along a surface of the tubular frame, wherein the coating is configured to inhibit tissue in-growth into the stent and spaced from an anchoring feature on the flared section, and wherein the anchoring feature is exposed to the GI tract to promote attachment to tissue along the GI tract; and positioning the flared section along one side of a GI tract target site, positioning the intermediate section directly adjacent the GI tract target site, and introducing fluid or therapeutic material through the ports during treatment.

11. The method of claim 10, further comprising determining a location of the GI tract target site, wherein the GI tract target site corresponds to a leak of the GI tract.

12. The method of claim 10, further comprising bypassing a portion of the GI tract using the intermediate section; and positioning the second end at a location distal to the GI tract target site.

13. The method of claim 12, further comprising securing the second end within the GI tract, such that fluid received at the first end is allowed to travel to the second end through the intermediate section.

* * * * *